United States Patent [19]

Spielvogel

[11] Patent Number: 5,266,359
[45] Date of Patent: Nov. 30, 1993

[54] LUBRICATIVE COATING COMPOSITION, ARTICLE AND ASSEMBLY CONTAINING SAME AND METHOD THEREOF

[75] Inventor: David E. Spielvogel, Springboro, Ohio

[73] Assignee: Becton, Dickinson and Company, Franklin Lakes, N.J.

[21] Appl. No.: 811,476

[22] Filed: Dec. 20, 1991

Related U.S. Application Data

[62] Division of Ser. No. 640,714, Jan. 14, 1991, abandoned.

[51] Int. Cl.$^5$ .................. B32B 15/02; B32B 15/08; B05D 1/18; A61M 25/01
[52] U.S. Cl. .................. 427/388.4; 427/2; 428/35.7; 428/35.8; 428/450; 424/422; 424/430; 523/113; 524/506; 525/100; 525/102
[58] Field of Search ............ 427/2, 388.4; 428/35.7, 428/35.8, 450; 523/113; 424/422, 430; 524/506; 525/100, 102

[56] References Cited

U.S. PATENT DOCUMENTS

| | | | |
|---|---|---|---|
| 4,413,086 | 11/1983 | Chang et al. | 524/506 |
| 4,490,416 | 12/1984 | Westall et al. | 528/17 |
| 4,614,675 | 9/1986 | Ona et al. | 528/33 |
| 4,631,208 | 12/1986 | Westall | 528/15 |
| 4,645,691 | 2/1987 | Ona et al. | 528/17 |
| 4,720,521 | 1/1988 | Spielvogel et al. | 524/588 |
| 4,844,986 | 7/1989 | Karakelle et al. | 427/2 |
| 4,981,757 | 1/1991 | Landers et al. | 427/388.4 |
| 5,019,096 | 5/1991 | Fox, Jr. et al. | 427/2 |
| 5,135,516 | 8/1992 | Sahatjian et al. | 427/2 |

FOREIGN PATENT DOCUMENTS 403400 5/1989 European Pat. Off. ............ 524/588

*Primary Examiner*—Paul R. Michl
*Assistant Examiner*—Andrew E. C. Merriam
*Attorney, Agent, or Firm*—Richard E. Brown

[57] ABSTRACT

A lubricating composition includes an emulsion of a noncuring polysiloxane, a surfactant and water. Preferred polysiloxanes include a polar group, most preferably an aminoalkyl or carboxylalkyl terminating group. Preferred surfactants are copolymers of polysiloxane and polyoxyethylene. A metal article such as a needle, blade, cannula or quidewire includes a coating of the polysiloxane and the surfactant which renders the article surface lubricious. The article may be in a sliding relationship with a plastic article in an assembly such as a catheter-quidewire or a catheter-cannula assembly. The plastic portion of the assembly may also include a lubricant. The invention includes a method of making the lubricated article.

11 Claims, 3 Drawing Sheets

LUBRICATIVE COATING COMPOSITION, ARTICLE AND ASSEMBLY CONTAINING SAME AND METHOD THEREOF

This is a division of application Ser. No. 07/640,714, filed Jan. 14, 1991, now abandoned.

BACKGROUND OF THE INVENTION

1. Field of the Invention

This invention relates to medical articles, and more particularly, relates to a lubricating composition, a metal article coated therewith and to a method for its preparation.

2. Background of the Invention

Many occasions arise when it is necessary to puncture the skin with a metal device, generally of steel, having a sharp point or edge. Representative of such devices are surgical blades, hypodermic needles, lancets, cannulas, catheter insertion devices, guidewires, stylets and the like. In other cases, a cutting edge, such as a razor blade, is advanced across a skin surface.

When such a device is advanced across the skin or inserted through the skin, the skin is stretched and a certain amount of pain is experienced. It has been common practice for many years to lubricate the device to minimize pain.

Noncuring, nonpolar silicones, such as the DC-360 ™ series of medical grade polydimethyl siloxanes (PDMS) available from Dow Corning Co. have been used. These products, while widely used, have the disadvantage of creeping or migrating from the surface to which they have been applied. Another problem with these lubricants is adhesion which develops over time when two plastic surfaces are engaged by an interference fit. For plastic syringes, Williams et U.S Pat. No. 4,767,414, discloses that plasma treatment of one of the surfaces and PDMS at the interface overcomes adhesion For a catheter cannula assembly, Williamitis et al. discloses in U.S. Pat. No. 4,664,657 that adhesion can be overcome if the PDMS is of high viscosity.

The problem of migration is particularly severe when metal surfaces are lubricated with noncuring PDMS. For example, in the case of a hypodermic needle coated with PDMS, the coating may be substantially removed due to frictional forces during penetration of the skin and vein, making subsequent removal of the needle difficult and painful to the patient. Migration during storage and inadvertent removal during processing is also a concern.

Spielvogel, in U.S. Pat. No. 4,720,521, discloses overcoming the migration problem by including a noncuring PDMS in a curing composition. The noncuring lubricating PDMS is occluded in a mixture of at least three curing silicones which adhere to a metal surface.

U.S. Pat. No. 3,574,673 to Schweiger discloses curing organopolysiloxanes used as friction reducing coatings on blades. These products are copolymers of alkylamine modified methoxysiloxanes which undergo room temperature moisture curing to a gelatinous film. Representative of this class of materials is the commercially available product MDX-4-4159. Depending on ambient humidity, MDX-4-4159 requires at least a four hour precure and from two to ten days for complete cure. In addition, solvent solutions used for dip application, because of the moisture curing, quickly turn cloudy due to precipitated polymer from reaction of the MDX-4-4159 with humidity in the air. Dipping solutions must be replaced frequently which is time consuming, wasteful and costly.

In U.S. Pat. No. 4,904,433, Williamitis discloses a method for catheter tipping which includes applying a noncuring aminoalkyl terminated polysiloxane to a catheter blank, mounting the coated blank on a mandrel, advancing the mandrel into a heated die for tipping and removing the tipped catheter from the die and the mandrel.

Since conventional lubricants are not water soluble, it has been standard practice in the art to apply lubricant coatings to articles from a solvent solution. A variety of solvents has been used, most of which are either inflammable or toxic. In recent years, fluorocarbons have come to the fore as the preferred solvents. These solvents, however, are now known to be a major contributor to the depletion of the atmosphere ozone layer. Accordingly, there is a need for a polysiloxane composition capable of lubricating metal surfaces which overcomes migration problems by adhering firmly and quickly without a need for cure time and which can be applied from a safe and environmentally acceptable solvent. The present invention addresses this need.

SUMMARY OF THE INVENTION

One aspect of the invention is a coating composition for an article comprising an aqueous emulsion of a surfactant and a noncuring polysiloxane lubricant substituted by a polar group, hereinafter referred to as the polar lubricant. Another aspect of the invention is an article, preferably a metal article, coated with the emulsion The article may have an edge for cutting, such as a blade, a point for puncturing, such as a needle or cannula, or it may be intended for sliding contact with the other surface, such as a stylet or guidewire. Preferred noncuring polar lubricants are polysiloxanes terminated with an amino or carboxyl group. The most preferred polar lubricant is an aminopropyl terminated polysiloxane of viscosity about 2,000. Preferred surfactants are copolymers of polysiloxane and polyoxyethylene.

In another aspect of the invention, a catheter assembly includes the lubricated guidewire or cannula and a mated plastic catheter tubing. The tubing may also be coated with the polar lubricant or preferably with a nonpolar polysiloxane lubricant. The preferred nonpolar lubricant for the catheter portion of the assembly is a trialkylsiloxy terminated polysiloxane.

The invention includes a method to prepare the lubricated article which includes preparing an aqueous emulsion of the polar lubricant and the surfactant, applying the emulsion to the article, and evaporating the water to leave the lubricant and surfactant on the article surface.

The metal article coated with the emulsified composition of the invention has improved lubricity compared to an article coated with a conventional lubricant. Because of the polar group, the lubricant is adsorbed into the metal and adheres to the surface so that wipe-away is significantly reduced. Thus, when the hypodermic needle of the invention is inserted through the skin, the lubricant is not wiped away to form a pool on the skin surface but instead remains adherent and is thus available as a lubricant when the needle is retracted. In contrast, a metal needle lubricated with a conventional lubricant suffers significant beading and wipe-away so that little is left for retraction. Significant pain is experienced by the patient due to the friction between the substantially bare needle and the skin. Similarly, other cutting devices, such as surgical blades, cannulas and lancets may be used with less pain for the patient due to the enhanced retention of the noncuring polar lubricant.

It is evident that articles intended for multiple use, such as razor blades, may also benefit from the noncuring polar lubricant of the composition. Currently used lubricants for blades are of polytetrafluoroethylene or fluorinated waxes which require high temperature curing or silicones which require moisture curing. The polar lubricant of the composition is noncuring, of low viscosity so that it remains a liquid, and is easily applied in a thin economical coating. Because of its adhering property, more shaves of greater comfort can be performed before the lubricant is removed and the blade loses its edge.

For metal articles used in sliding contact with a plastic surface, such as catheter quidewires, the noncuring polar lubricant overcomes the adhesion which routinely develops during shelf time. Thus, after catheter placement, the quidewire may easily be removed without application of excess force to overcome the adhesion, which, with conventional lubricants, often leads to sudden movement, loss of catheter placement and danger to the patient.

By emulsifying the polar lubricant in an aqueous system, a method to lubricate metal articles which does not involve toxic or flammable solvents is provided. In particular, the emulsion of the invention avoids the use of ozone-damaging fluorocarbon solvents and thus also provides environmental advantages over conventional lubricants.

DETAILED DESCRIPTION

Figure 1:
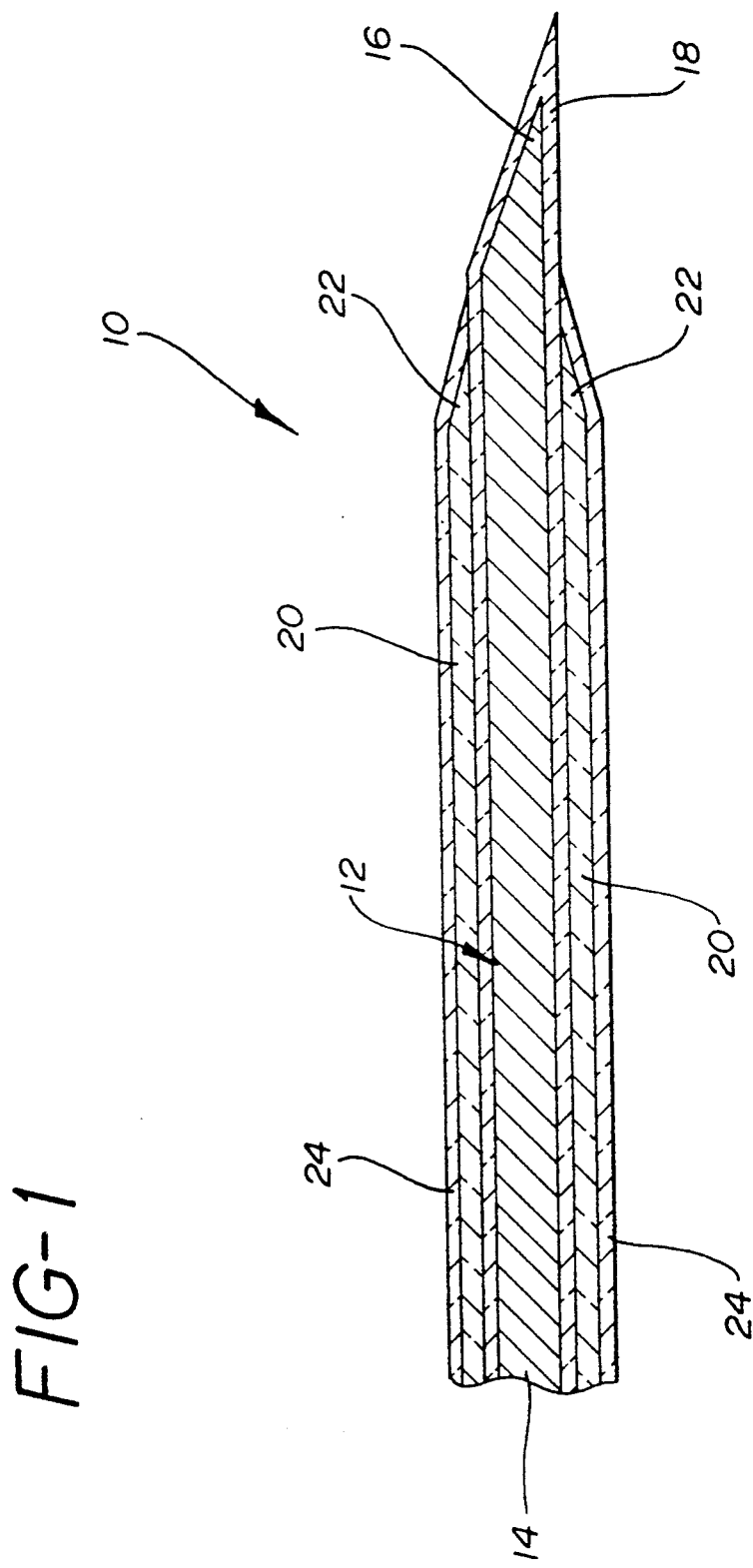
FIG. 1 illustrates a lubricated catheter assembly of the invention including a cannula and catheter tubing.

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

One aspect of the invention is a lubricative coating composition which includes an emulsion of a noncuring polysiloxane, a surfactant and water.

In one embodiment of the composition, the noncuring polysiloxane is nonpolar. The nonpolar noncuring polysiloxane may be, for example, a conventional trialkylsiloxy terminated polysiloxane, most preferably a trimethylsiloxy terminated polydimethylsiloxane. These products are well-known and a wide variety of products ranging in viscosity from 0.65 to 2,500,000 are commercially available from Petrarch Systems. Particularly preferred nonpolar noncuring lubricants are the DC®360 medical grade polydimethylsiloxanes ranging in viscosity from 350 to 12,500 commercially available from Dow Corning Corp., Midland, Michigan. The most preferred nonpolar lubricant is DC®360 fluid of viscosity 12,500.

Preferred noncuring polysiloxane lubricants have a polar group. The polar group may be terminal or pendant. Preferred polar lubricants contemplated by the present invention are noncuring polysiloxanes terminated by the polar group, and may be represented by the formula

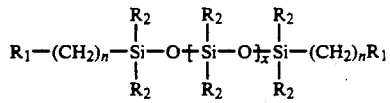

wherein $R_1$ may be OH, $NH_2$,

and COOH, $R_2$ may be lower alkyl of 1 to 4 carbon atoms, n may be 2 to 4, and x is an integer sufficient to give the lubricant a viscosity of about 10 to 2,000,000 ctsk. In preferred lubricants, $R_1$ is $NH_2$ or COOH, $R_2$ is $CH_3$ and the viscosity is 100 to 100,000 ctsk. The most preferred lubricants are aminopropyl terminated polydimethyl siloxanes of viscosity 300 to 25,000 ctsk and carboxypropyl terminated polydimethyl siloxanes of viscosity 800 to 25,000 ctsk. These products, known in the art as intermediates for polymer synthesis, are commercially available from General Electric or from Petrarch Systems, Bristol, Pennsylvania. The invention will henceforth be described in terms of the commercial aminopropyl terminated Petrarch product PS 513 of viscosity 2,000 ctsk, and the carboxypropyl terminated products Petrarch PS 563 and General Electric 104-3199.

The noncuring lubricant may be emulsified in water in combination with one or more surfactants. Any surfactant as known in the art which forms stable aqueous emulsions with the noncuring lubricant is contemplated to fall within the scope of the invention. Thus, without wishing to be limited thereby, suitable surfactants are polyoxyethylene alcohols, polyoxyethylene ethers of alkylphenols and polyoxyethylene esters of fatty acids. Preferred surfactants are fatty acid esters of sorbitol (SPAN TM) and polyoxyethylene derivatives of sorbitol (TWEEN TM). The most preferred surfactants are copolymers of polyoxyethylene with polysiloxane. These products are well known and most are commercially available.

The noncuring lubricant and surfactant may be emulsified with water by any conventional high speed mixing procedure. For example, a homogenizer or a blender may be used to prepared emulsions at high solids content (20 to 40 weight percent) and diluted with water by mixing to achieve a typical coating concentration (0.5 to 5 weight percent). Alternatively, the emulsions may be prepared at the low solid concentrations (0.5 to 5%) and used without further dilution. The final coating concentration of the lubricant and surfactant in the composition may be about 1 to 4 weight percent of each.

If desired, an antimicrobial agent may be added to the composition prior to coating the article. Suitable antimicrobial agents are, for example, chlorhexidine, methyl paraben, phenol and the like. A concentration of about 0.1 to 10, preferably above 3 to 5% by weight of the agent may be included in the composition.

The article of the invention may be plastic or preferably metal. While the invention contemplates lubrication of any metal article, preferred articles are steel such as carbon steel, most preferably stainless steel. It is believed, although not yet substantiated, that the preferred polar lubricant, while noncuring, is adherent to the article because the polar group causes adsorption of the lubricant into the article surface.

Representative nonlimiting metal articles contemplated to be lubricated with the polar lubricant of the invention are blades such as scalpels, razor blades and surgical blades, hypodermic needles, such as syringe needles, lancets and any metal catheter insertion device. The term catheter insertion device is intended to include devices for skin puncture and catheter placement. The skin puncture device may be a cannula or a catheter needle portion which is unitary with a plastic catheter tubing. The term cannula will hereinafter be used generically to define any metal device for skin puncture used with a catheter tubing. The term catheter placement device includes any metal device, such as a quidewire or a stylet used to advance or position a catheter tubing after insertion. The term quidewire will hereinafter be used generically to define catheter placement devices.

In one preferred embodiment of the invention, the metal article includes a cutting edge. Thus, the article of the invention may be a razor blade, a surgical blade or a scalpel having the composition coated thereon.

Another preferred embodiment is a metal article having a cutting point for puncture of a membrane, preferably skin. Preferred article for this embodiment of the invention are hypodermic needles, lancets, cannulas and the like coated with the composition.

It is not intended that the metal articles which fall within the scope of the invention be limited to cutting or puncturing devices. Thus, a preferred article is a catheter guidewire coated with the composition. For this embodiment of the invention, a coated cannula portion of a catheter assembly of the invention may be used to puncture the skin of a patient and the catheter portion then inserted at the puncture site. After removal of the cannula, the coated guidewire of the invention may be passed down the catheter and used to advance or position the catheter to the desired location in a patient's vein or artery.

The catheter portion, preferably of plastic, of the catheter assembly may also be lubricated with the composition or preferably with a coating of the noncuring nonpolar lubricant described above. Any suitable polymer as known in the art may be used for the catheter portion of the assembly. Without being limited thereby, the catheter may be of polyolefin, polyvinyl, polyester, polyamide and preferably polyurethane.

While the composition including a polar lubricant is the most effective lubricant on the metal article, it has been found that a noncuring nonpolar polysiloxane is the most effective lubricant on plastic articles. Thus, the most preferred assembly of the invention includes a cannula coated with the composition containing the polar lubricant positioned inside a plastic catheter tubing having a coating of the composition containing the nonpolar lubricant on the outside surface thereof.

FIG. 1 illustrates one embodiment of an assembly 10 of the invention. A steel cannula 12 has a body portion 14 and a tip 16. Tip 16 and preferably at least part of body portion 14 have a coating 18 of the polar lubricant thereon. The coated cannula fits inside of a plastic catheter tubing 20. In general, the catheter is two gauge sizes larger than the cannula. Catheter tubing 20 preferably has a taper 22 at its forward end for additional patient comfort during insertion through the puncture site formed by tip 16. A coating 24 of the composition containing the nonpolar lubricant on tubing 20 provides patient comfort during insertion and withdrawal of the catheter through the puncture site.

The composition may be applied to the article by any conventional procedure such as wiping, spraying, roll coating, printing or preferably by dipping. After application of the composition to the article, the water component of the emulsion may be removed by any suitable evaporative method, such as air drying, preferably augmented by mild heating.

The thickness of the coating may be varied depending on the concentration of the components in the emulsified composition, the temperature of application, the time of residence of the article in the emulsion and the rate of withdrawal from the emulsion and may be about 10 to 500, preferably 30 to 500, most preferably about 50 to 300 $\mu$ in thickness.

The lubricating effectiveness of the composition may be tested for penetration, drag and retract forces using a Model 1122 Instron Universal Testing Machine. The drag force is the frictional force between the needle and the membrane after the needle has punctured the membrane and is continued to be moved in relation to the membrane. The retract force is the force required to slide the needle surface through the membrane when withdrawing the needle.

The following examples are provided to further describe the invention but are not to be considered as limitative of the invention.

EXAMPLE I

Preparation of Lubricative Composition

A. Aminopropyl terminated polysiloxane lubricant of viscosity 2,000 ctsk, 30 (Petrarch PS-513); polyoxyethylene polysiloxane copolymer surfactant (molecular weight 2,000 viscosity 300 ctsk ), 1.5 q; and water, 68.5 q were homogenized in a Fisher portable homogenizer to give a stable emulsion containing 4% by weight of solids. The emulsion was prepared using four passes through the homogenizer.

B. In the same way, an emulsion of carboxypropyl terminated polysiloxane lubricant of viscosity 600 to 800 (General Electric 104-3199) was prepared.

EXAMPLE II

Forty-eight 16 gauge stainless steel needles were divided into six groups of 8 each and treated as follows:
(1) as received
(2) dipped into 1,1,1-trichloroethane
(3) dipped into a 4% solution of PS 513 in 1,1,1-trichloroethane
(4) dipped into the emulsion of Example IA
(5) dipped into a 4% solution of GE 104-3199 in 1,1,1-trichloroethane
(6) dipped into the emulsion of Example IB All needles were withdrawn from the dipping baths at a rate of 10ft/min, heated 10 minutes at 200° C. and set aside at room temperature overnight with protection from dust. The needles were affixed to the Instron and rubber membrane, drag and retract were measured. The averaged forces are given in the table.

| Group | Force, newtons | | |
| --- | --- | --- | --- |
| | Penetration | Drag | Retract |
| 1 | 2.9 ± .12 | 2.4 ± .09 | 2.0 ± .12 |
| 2 | 2.8 ± .28 | 2.4 ± .21 | 1.9 ± .20 |
| 3 | 1.4 ± .09 | 0.46 ± .04 | 0.42 ± .02 |
| 4 | 1.5 ± .05 | 0.34 ± .05 | 0.38 ± .02 |
| 5 | 2.1 ± .15 | 0.46 ± .04 | 1.44 ± .29 |
| 6 | 1.9 ± .08 | 0.44 ± .03 | 1.51 ± .10 |

It is seen from the table that the emulsions give forces which are lower than the control forces and comparable to the forces measured for the solvent applied lubricants.

EXAMPLE III

Twenty number 10 Bard Parker carbon steel surgical blades were divided into four groups of five each and treated as follows:
(1) dipped into a 4% solution of PS 513 in 1,1,1-trichloroethane;
(2) dipped into the emulsion of Example IA;
(3) dipped into a 4% solution of PS 563 in 1,1,1-trichloroethane;
(4) dipped into a 4% emulsion of PS 563 prepared in accordance with Example IA.

Figure 2:
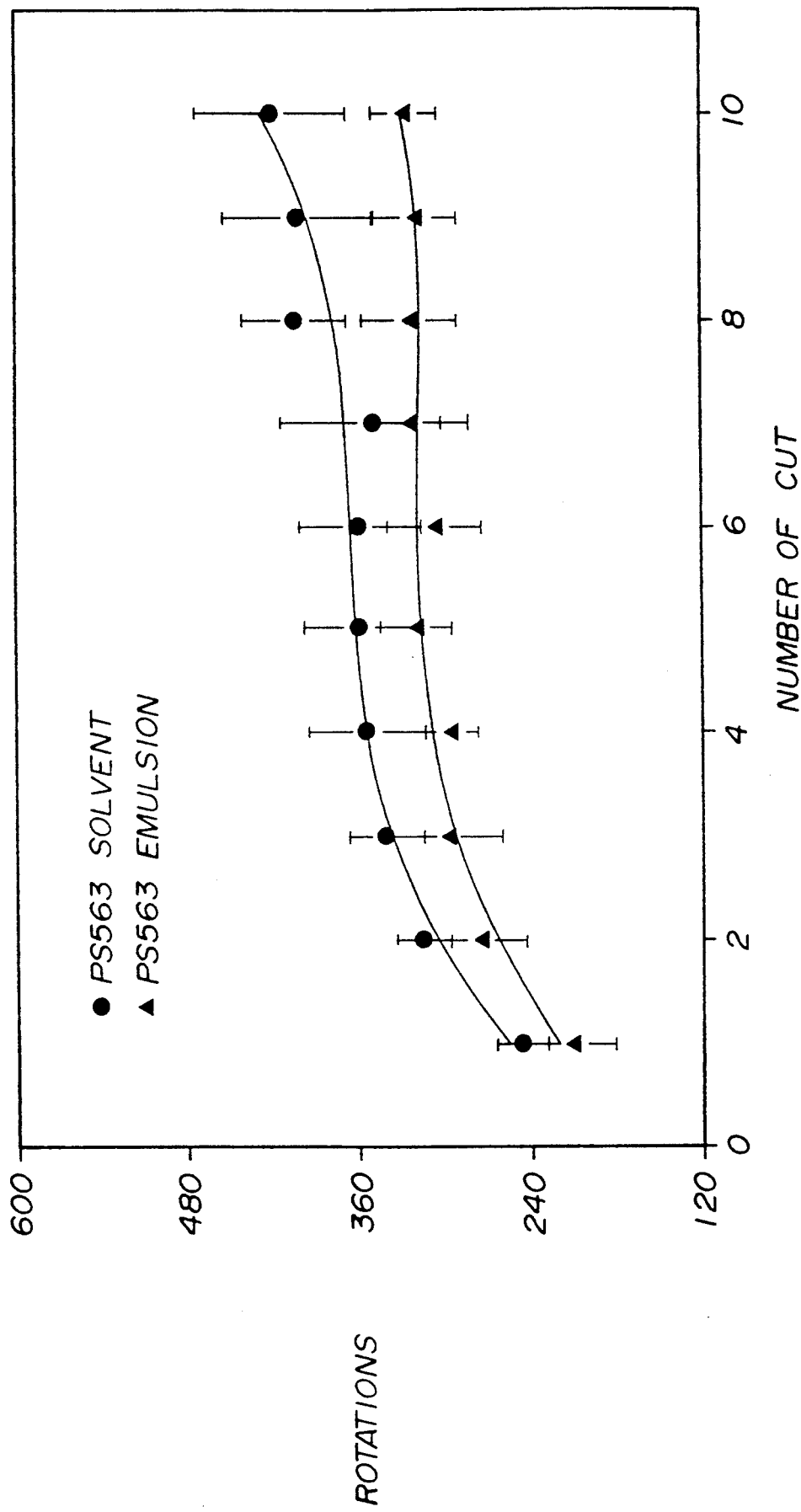
FIGS. 2 and 3 compare blade sharpness after coating with the emulsion of the invention and with the same lubricants coated from a solvent.
Figure 3:
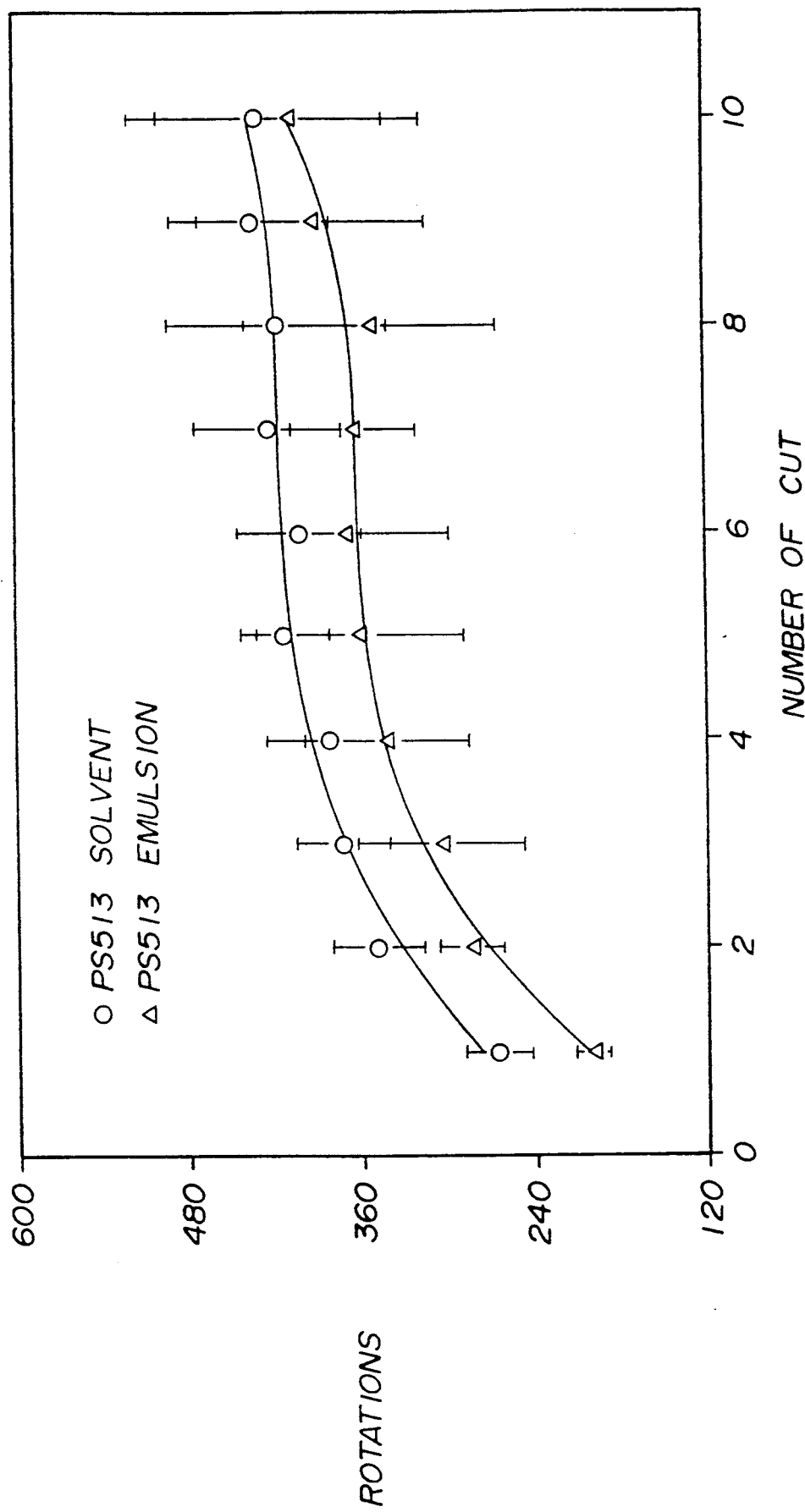

The blades were tested for sharpness by affixing them to a pivot arm and positioning them adjacent to a 1/16 inch thick latex rubber tubing mounted on a spindle rotating at constant speed. The number of spindle rotations required to cut through the tubing was electronically counted. Ten tubing sections were cut consecutively and the number of rotations required was counted and plotted in FIGS. 2 and 3.

The Figures show improved sharpness of blades coated with the emulsion of the invention compared to coatings of the same lubricants applied from a 1,1,1-trichloroethane solution.

What is claimed is:

1. A metal article having thereon a lubricious coating comprising a noncuring polysiloxane lubricant selected from the group consisting of the formula

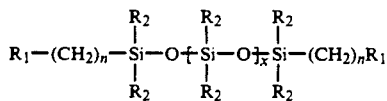

wherein $R_1$ is $NH_2$ $NHR_2$ or $COOH$, $R_2$ is lower alkyl of 1 to 4 carbon atoms, n is 2 to 4, and x is an integer sufficient to give the lubricant a viscosity of about 10 to 2,000,000 centistokes, and a polyoxyethylene polysiloxane copolymer surfactant.

2. The article of claim 1 which is a guidewire.
3. The article of claim 1 which is a cannula.
4. The article of claim 1 which is a blade.
5. The article of claim 1 which is a needle.
6. The article of claim 1 wherein said coating further comprises an antibacterial agent.
7. A metal article having thereon a coating comprising a noncuring aminopropyl terminated polysiloxane lubricant selected from the group consisting of the formula

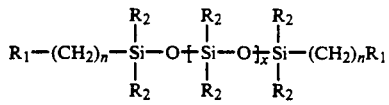

wherein $R_1$ is $NH_2$ $NHR_2$ or $COOH$, $R_2$ is lower alkyl of 1 to 4 carbon atoms, n is 2 to 4, and x is an integer sufficient to give the lubricant a viscosity of about 10 to 2,000,000 centistokes, and a polyoxyethylene polysiloxane copolymer surfactant.

8. A method for lubricating a metal article comprising:
a) providing an emulsified lubricating composition which includes water, a polyoxyethylene polysiloxane copolymer surfactant and a polysiloxane lubricant selected from the group consisting of the formula

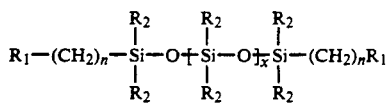

wherein $R_1$ is $NH_2$ $NHR_2$ or $COOH$, $R_2$ is lower alkyl of 1 to 4 carbon atoms, n is 2 to 4, and x is an integer sufficient to give the lubricant a viscosity of about 10 to 2,000,000 centistokes;
b) applying a coating of said composition onto a surface of a metal article; and
c) removing said water from the coated metal surface to give a lubricated surface.

9. The method of claim 8 wherein said applying is performed by dipping said article into said composition.

10. The method of claim 8 wherein said applying step is performed by spraying said composition onto said article.

11. A method for lubricating a metal article comprising:
a) providing an emulsified lubricating composition which includes water, a polyoxyethylene polysiloxane copolymer surfactant and an aminopropyl terminated polysiloxane lubricant selected from the group consisting of the formula

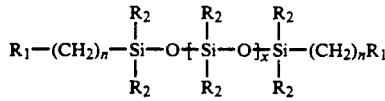

wherein $R_1$ is $NH_2$, $R_2$ is lower alkyl of 1 to 4 carbon atoms, n is 2 to 4, and x is an integer sufficient to give the lubricant a viscosity of about 10 to 2,000,000 centistokes;
b) dipping a metal article into said composition;
c) withdrawing said article from said composition to give a coating on said article; and
d) evaporating the water from the coating on the article to give a lubricated surface.

* * * * *